(12) United States Patent
Chretien et al.

(10) Patent No.: US 9,605,203 B2
(45) Date of Patent: Mar. 28, 2017

(54) COMPOSITION PREVENTING THE POLYMERIZATION OF ETHYLENICALLY UNSATURATED MONOMERS AND THE REMOVAL THEREOF BEFORE POLYMERIZATION

(71) Applicant: RHODIA OPERATIONS, Paris (FR)

(72) Inventors: Christelle Chretien, Villeurbanne (FR); Lars Fischer, Vienne (FR); Stephan Verdier, Lyons (FR); Jacques Cavezzan, Villeurbanne (FR)

(73) Assignee: Rhodia Operations, Paris (FR)

( * ) Notice: Subject to any disclaimer, the term of this patent is extended or adjusted under 35 U.S.C. 154(b) by 0 days.

(21) Appl. No.: 15/021,994

(22) PCT Filed: Sep. 11, 2014

(86) PCT No.: PCT/EP2014/069438
§ 371 (c)(1),
(2) Date: Mar. 15, 2016

(87) PCT Pub. No.: WO2015/039954
PCT Pub. Date: Mar. 26, 2015

(65) Prior Publication Data
US 2016/0230089 A1 Aug. 11, 2016

(30) Foreign Application Priority Data
Sep. 19, 2013 (FR) ...................... 13 02178

(51) Int. Cl.
| | | |
|---|---|---|
| C07C 39/08 | (2006.01) | |
| C08F 36/00 | (2006.01) | |
| C09K 15/08 | (2006.01) | |
| C08F 236/08 | (2006.01) | |
| C08F 136/08 | (2006.01) | |
| C07C 37/68 | (2006.01) | |
| C08F 2/38 | (2006.01) | |
| C07C 37/14 | (2006.01) | |
| C07C 37/82 | (2006.01) | |
| C07C 37/74 | (2006.01) | |

(52) U.S. Cl.
CPC .............. *C09K 15/08* (2013.01); *C07C 39/08* (2013.01); *C08F 136/08* (2013.01); *C08F 236/08* (2013.01); *C07C 37/14* (2013.01); *C07C 37/68* (2013.01); *C07C 37/74* (2013.01); *C07C 37/82* (2013.01); *C08F 2/38* (2013.01)

(58) Field of Classification Search
CPC .......... C07C 39/08; C07C 37/14; C07C 37/68; C07C 37/74; C07C 37/82; C09K 15/08; C08F 2/38; C08F 36/00
See application file for complete search history.

(56) References Cited

U.S. PATENT DOCUMENTS

| | | | | |
|---|---|---|---|---|
| 3,656,980 A * | 4/1972 | Harada | .................... | C07C 39/08 106/285 |
| 4,370,506 A * | 1/1983 | Ancillotti | ................ | C07C 37/16 568/784 |
| 4,466,904 A * | 8/1984 | Watson | ..................... | C07C 7/20 252/402 |
| 4,547,619 A * | 10/1985 | Diaz | ......................... | C07C 7/12 208/91 |
| 2005/0115820 A1 | 6/2005 | Mathieu | | |

FOREIGN PATENT DOCUMENTS

| | | | | | |
|---|---|---|---|---|---|
| CN | 101012155 A | * | 8/2007 | ............ | C07C 37/14 |
| CN | 101955411 A | * | 1/2011 | ............ | C07C 15/46 |
| CN | 102531848 A | * | 7/2012 | ............ | C07C 37/16 |
| CN | 102603490 A | * | 7/2012 | ............ | C07C 39/08 |
| GB | 1130188 | * | 10/1968 | ............ | C07C 39/08 |
| JP | 49-127932 A | * | 12/1974 | | |
| JP | 62-64810 A | * | 3/1987 | ............ | C08F 236/10 |
| JP | 2-152939 A | * | 6/1990 | ............ | C07C 39/08 |
| JP | 4-273838 A | * | 9/1992 | ............ | C07C 39/08 |
| JP | 6-73105 A | * | 3/1994 | ............ | C08F 2/00 |
| JP | 7-82197 A | * | 3/1995 | ............ | C07C 39/08 |
| JP | 2003-73317 A | * | 3/2003 | ............ | C07C 37/60 |
| WO | WO 98/59016 A1 | | 12/1998 | | |
| WO | WO 03/068713 A1 | | 8/2003 | | |
| WO | WO 2006/078123 A1 | * | 7/2006 | ............ | C08F 2/38 |

\* cited by examiner

*Primary Examiner* — Rip A Lee

(57) ABSTRACT

The invention describes a composition that inhibits the polymerization of ethylenically unsaturated monomers, including at least 98% by weight of 4-tert-butylcatechol (4-TBC), 0.03% to 0.2% by weight of catechol (PC), and at least one impurity selected among 3-tert-butylcatechol, tert-butylhydroquinone, 3,5-di-tert-butylcatechol and mixture thereof, the total quantity of said impurities and of the PC being 0.1% to 0.8% by weight of said composition. The invention also describes a method for removing said polymerization-inhibiting composition present in a mixture including at least one ethylenically unsaturated monomer.

17 Claims, No Drawings

COMPOSITION PREVENTING THE POLYMERIZATION OF ETHYLENICALLY UNSATURATED MONOMERS AND THE REMOVAL THEREOF BEFORE POLYMERIZATION

This application is a U.S. national stage entry under 35 U.S.C. §371 of International Patent Application No. PCT/EP2014/069438, filed Sep. 11, 2014, which claims priority to French Patent Application Nos. FR 1302178, filed on Sep. 19, 2013, the whole content of each of these applications is hereby incorporated herein by reference for all purposes.

The present invention relates to the field of compositions for preventing the polymerization of monomers bearing an ethylenic unsaturation, in particular butadiene and isoprene, and also to the field of removal of said compositions before performing polymerization.

4-tert-Butylcatechol (4-TBC) is known to be an efficient inhibitor for preventing the polymerization of ethylenically unsaturated monomers. In the field of polymerization, it is preferable to remove the monomer-polymerization inhibitors before commencing the step of initiation of polymerization. Specifically, the presence of inhibitors in the monomers, during polymerization, is detrimental since the inhibitors react with the polymerization catalyst, leading to reduced performance in terms of activity and selectivity. Also, the need to improve the capacity for removing the inhibitors, present in monomers before initiating the polymerization, is an ongoing need. Removal of the inhibitors present in monomers is conventionally performed by distillation, by washing using an alkaline solution or alternatively by adsorption onto an inorganic solid. Now, one of the main constraints for performing the removal of inhibitors lies in the composition of the inhibitor itself. The inhibitor compositions known to date based on 4-TBC rarely produce satisfactory performance since they often require, for their own removal, the application of substantial means, for example the need for large volumes of alkaline solution and the need to treat the effluents when the removal is performed by washing, or alternatively the need for a large amount of adsorbent when the removal is performed by adsorption.

The present invention proposes to overcome the above drawbacks by providing a novel inhibitor composition based on 4-tert-butylcatechol which has a given impurity profile. Said novel composition efficiently inhibits the polymerization of ethylenically unsaturated monomers. It has been found, surprisingly, that the removal of said inhibitor composition according to the invention, present in a monomer, is substantially improved over that of compositions existing on the market. In particular, it has been found that the removal of said inhibitor composition according to the invention requires substantially fewer washing steps than those required by the known inhibitor compositions, which is favorable in terms of volume of alkaline solution to be used and of effluent to be treated. It has also been found that the removal of said inhibitor composition according to the invention requires a substantially reduced amount of adsorbent when compared with that required by the known inhibitor compositions, which reduces the need to regenerate the adsorbent and consequently increases the lifetime of the adsorbent.

The subject of the present invention is a composition for inhibiting the polymerization of ethylenically unsaturated monomers, comprising:
  at least 98% by weight of 4-tert-butylcatechol (4-TBC),
  from 0.03% to 0.2% by weight of catechol (PC),
  at least one impurity chosen from 3-tert-butylcatechol (3-TBC), tert-butylhydroquinone (TBHQ) and 3,5-di-tert-butylcatechol (diTBC) and a mixture thereof, the total amount of said impurities and of the PC representing from 0.1% to 0.8% by weight of said composition.

It is recalled that catechol corresponds to 1,2-dihydroxybenzene.

In accordance with the invention, the composition according to the invention comprises catechol as impurity in a content of between 0.03% and 0.2% by weight, preferably between 0.03% and 0.1% by weight. The composition according to the invention also comprises one or more additional impurities chosen from 3-tert-butylcatechol (3-TBC), tert-butylhydroquinone (TBHQ) and 3,5-di-tert-butylcatechol (diTBC). Said composition advantageously comprises at least two of said impurities chosen from 3-TBC, TBHQ and diTBC. More preferably, it comprises said three impurities such that the composition of the invention comprises catechol, 3-TBC, TBHQ and diTBC. Advantageously, said composition comprises at least the impurity diTBC and at least the impurity PC.

In accordance with the invention, the total amount of the impurities 3-TBC, PC, TBHQ and diTBC represents from 0.1% to 0.8% by weight of the composition. More precisely, the impurity 3-TBC, when it is present in the composition, represents from 0.02% to 0.1% by weight. The impurity TBHQ, when it is present in the composition, represents from 0.003% to 0.005% by weight. The impurity diTBC, when it is present in the composition, represents from 0.1% to 0.6% by weight, preferably from 0.15% to 0.5% by weight.

According to a particular mode of the invention, additives may be added to the inhibitor composition. The additive-supplemented composition comprises one or more additives chosen from dispersants, detergents, antioxidants, antifoams, rust inhibitors and corrosion inhibitors. The additives advantageously represent from 0.1% to 90% by weight and preferably from 1% to 60% by weight of the additive-supplemented composition. The dispersants are advantageously chosen from sulfonates, phosphates, esters, amines and succinimides. The detergents are advantageously chosen from salicylates, phenates and sulfonates. The antioxidants are advantageously chosen from amines and phenol derivatives. The antifoams are advantageously chosen from silicones and acrylates. The rust inhibitors are advantageously chosen from amines, esters, phenol derivatives and sulfonates. The corrosion inhibitors are advantageously chosen from nitrogen compounds such as triazoles and thiadiazoles. The additive-supplemented composition may be in solid form or in liquid form. A solvent may be added to this additive-supplemented composition.

In accordance with the invention, the composition based on 4-TBC inhibits the polymerization of ethylenically unsaturated monomers. Said monomers are advantageously chosen from monoolefins and diolefins, particularly diolefins bearing conjugated double bonds, vinyl monomers (i.e. compounds comprising at least one vinyl group), cyclopentadiene and dicyclopentadiene. More particularly, the composition according to the invention is effective for inhibiting the polymerization of styrene and derivatives thereof such as alpha-methylstyrene, vinyltoluene and divinylbenzene, acrylic acid and esters thereof such as methyl acrylate, ethyl acrylate and butyl acrylate, methacrylic acid esters such as methyl methacrylate, methyl vinyl ketone, acrylonitrile, isoprene, 2,3-dimethylbuta-1,3-diene, 1,3-butadiene, chloroprene, bromoprene, 1-chlorobutadiene, vinyl chloride and 1,3-pentadiene. More preferably, the composition according to the invention is advantageously suitable for inhibiting the polymerization of 1,3-butadiene, isoprene and styrene.

The composition of the invention is prepared by reacting catechol with isobutene or tert-butanol in the presence of an acidic catalyst, for example bis-trifluoromethane sulfonamide, bis-pentafluoroethane sulfonamide and tris(trifluoromethanesulfonyl)methane. Isobutene or tert-butanol is used in a proportion of 0.01 to 50 equivalents per 1 equivalent of catechol. An amount of acidic catalyst of less than or equal to 0.01 equivalent per 1 equivalent of catechol is generally used. The reaction may be performed in the liquid phase or in a two-phase manner. It is performed at atmospheric pressure, at a higher or lower pressure, and at a temperature of between 0 and 150° C. It is performed according to a batch or continuous process. The mixture obtained on conclusion of the reaction is purified via any method known to those skilled in the art, in particular by extraction, by crystallization, by distillation or by precipitation so as to obtain the composition according to the invention.

It may be advantageous to add one or more solvents, for example methanol, water and/or toluene, to the composition of the invention. A subject of the present invention is also an inhibitor solution comprising the inhibitor composition as described above and at least one solvent. The solvent may be chosen from the group consisting of methanol, water and toluene, and mixtures thereof, for example a mixture of methanol and toluene. The solvent may represent from 5% to 95% by weight of the inhibitor solution, more preferably from 10% to 80% and even more preferably from 12% to 70%. According to one embodiment, the inhibitor solution comprises:

from 70% to 95% by weight of inhibitor composition according to the invention;
from 5% to 30% by weight of water or methanol.

According to another embodiment, the inhibitor solution comprises:

from 35% to 65% by weight of inhibitor composition according to the invention;
from 35% to 65% by weight of toluene.

The inhibitor solution may also contain one or more additives. The additives may be chosen from the group constituted by dispersants, detergents, antioxidants, antifoams, rust inhibitors and corrosion inhibitors.

A subject of the present invention is also a mixture comprising an ethylenically unsaturated monomer and the composition according to the invention. Said mixture is in various forms, depending on the form presented by the monomer. It may be a mixture in liquid form at room temperature or a gas/liquid two-phase mixture.

Said ethylenically unsaturated monomer is chosen from those listed above.

Said mixture preferentially comprises from 5 to 10 000 ppm of said composition according to the invention. It may also comprise one or more solvents, especially water, toluene or methanol.

Said mixture is stabilized by the presence of said composition which has an inhibitory effect on the polymerization of said ethylenically unsaturated monomer.

The mixture according to the invention may be prepared, for example, by mixing in any order said monomer, said composition and the solvent.

A subject of the present invention is also a process for removing said polymerization-inhibiting composition according to the invention present in a mixture comprising at least one ethylenically unsaturated monomer, said mixture being that described above. Said removal process is performed prior to the use of said monomer in a polymerization process.

A first embodiment of the removal process according to the invention consists in placing said composition for inhibiting the polymerization of ethylenically unsaturated monomers in contact with at least one solid inorganic oxide. Said organic oxide acts as an adsorbent onto which said inhibitor composition is adsorbed. Said removal process according to said first embodiment is thus based on the principle of adsorption. Said organic oxide is preferentially chosen from aluminas, silicas and silica-aluminas. Preferably, said organic oxide is an alumina. Any type of alumina is suitable for performing said process, in particular microporous, mesoporous or macroporous aluminas. The various types of alpha, beta and gamma crystal structures are also suitable.

Advantageously, said adsorption process is performed at room temperature. Said inorganic oxide is preferentially subjected beforehand to a heat treatment at a temperature advantageously between 200 and 400° C.

The performance of said first embodiment of the removal process according to the invention is measured by revealing a rupture point corresponding to the time after which the adsorbent begins to no longer fulfil its role as an adsorbent. The higher the rupture point, the more efficient said process of removal by adsorption, i.e. it requires a reduced amount of adsorbent relative to that required by a prior inhibitor composition to remove the same amount of inhibitor composition.

A second embodiment of the removal process according to the invention consists in washing with an alkaline solution said mixture comprising at least one ethylenically unsaturated monomer and said polymerization-inhibiting composition. Preferably, said alkaline solution is an aqueous solution of sodium hydroxide, especially of caustic soda, or an aqueous solution of potassium hydroxide.

Said removal process according to said second embodiment is thus based on the principle of absorption of the inhibitor composition by washing, said composition being found, after separation of the organic and aqueous phases, in said aqueous phase formed from said alkaline solution.

The performance of said second embodiment of the removal process according to the invention is measured by the number of washes that may be performed by the same alkaline solution without the inhibitor composition remaining in the monomer.

A third embodiment of the removal process according to the invention consists in distilling said mixture. Distillation of said mixture is performed in a conventional manner for a person skilled in the art.

A subject of the present invention is also a process for polymerizing ethylenically unsaturated monomers, comprising a step of removal of said inhibitor composition performed according to one of the embodiments described above, followed by at least one step of initiating polymerization. Said polymerization process is performed conventionally under standard conditions known to those skilled in the art of polymerizing ethylenically unsaturated monomers.

The invention will be understood more clearly in the light of the following examples, which are proposed as illustrations.

EXAMPLE 1

Preparation of Various Polymerization-Inhibiting Compositions 50 g of catechol and a catalytic amount of bis-trifluoromethane sulfonamide are successively placed in a 170 ml reactor. The reaction mixture is purged with nitrogen, heated to a temperature of 120° C. and then stirred. A pressure of 1 bar of isobutene is then applied and the reaction is stopped when about 11 g of isobutene have been consumed. On conclusion of the reaction, the mixture obtained is purified under conditions such that the various compositions A, B and C may be obtained. Compositions A, B and C contain 4-TBC and the impurities described in Table 1 below.

|  | Total content of impurities | PC (wt %) | 3-TBC (wt %) | diTBC (wt %) | TBHQ (wt %) |
| --- | --- | --- | --- | --- | --- |
| Composition A (invention) | 0.70 | 0.1 | 0.1 | 0.5 | 0.0045 |
| Composition B (comparative) | 0.62 | 0.009 | 0.01 | 0.60 | 0.002 |
| Composition C (comparative) | 0.861 | 0.001 | 0.15 | 0.65 | 0.06 |

The inhibition performance of compositions A, B and C was validated on isoprene:

Three 10 ml tubes were filled with a solution of isoprene and 20 ppm of TBC, provided, respectively, by compositions A, B and C. The tubes were sealed and placed in a bath at 100° C. for 16 hours. After 16 hours, the isoprene was evaporated from each tube at 50° C. and dried at 35° C. under reduced pressure. The degree of conversion of the isoprene into polymer was determined in each tube.

It was found that these degrees of conversion were equivalent in the three tubes. Compositions A, B and C thus have comparable inhibition performance.

EXAMPLE 2

Removal of the Inhibitor Compositions A, B and C by Washing with Sodium Hydroxide Each of said compositions A, B and C is present in an isoprene-based mixture.

The operating protocol for removing each of said compositions A, B and C present in the isoprene is as follows:
1—3 g of a sodium hydroxide solution are placed in a separating funnel.
2—10 g of an isoprene-inhibitor composition solution are added, the content of the inhibitor composition being equal to 1000 ppm.
3—After stirring, the whole is allowed to separate by settling until two phases separate out: the organic phase containing isoprene at the top and the aqueous phase with the inhibitor composition at the bottom.
4—A sample of the upper phase is taken and analyzed by high-performance liquid chromatography (HPLC). The amount of 4-TBC in the isoprene is measured.
5—The aqueous phase based on sodium hydroxide is recovered for recycling in a new washing step.
6—This procedure is repeated using in each washing step the same sodium hydroxide solution as that used during the first washing step (recycling of the sodium hydroxide solution) and a new isoprene-inhibitor composition solution having the same formulation as that stated in point 2 above. This procedure is repeated until the sodium hydroxide solution is no longer effective in removing the inhibitor composition from the isoprene.

The results obtained with the inhibitor compositions A, B and C are given in Table 2 below.

TABLE 2 performance in removing the inhibitor compositions A, B and C by washing with sodium hydroxide

| Inhibitor composition | A (invention) | B (comparative) | C (comparative) |
| --- | --- | --- | --- |
| Number of washing steps with the same NaOH solution | 1.2N | N | N |

The inhibitor compositions B and C make it possible to perform N washing steps effectively. The results demonstrate that the number of washing steps with the same NaOH solution is increased by 20% by using the inhibitor composition A. Thus, the use of inhibitor composition A makes it possible to limit the volumes of alkaline solution used for removing the inhibitor composition, particularly 4-TBC, present in the isoprene.

EXAMPLE 4

Removal of the Inhibitor Compositions A, B and C by Adsorption on Alumina

Each of said compositions A, B and C is present in an isoprene-based mixture.

The operating protocol for removing each of said compositions A, B and C present in the isoprene is as follows:
1—50 g of alumina (AxSorb 920, Axens) are placed in a glass column.
2—Once the alumina has been packed, an isoprene solution (300 ml) is placed over the alumina. The upper level of the isoprene solution is noted so that it remains unchanged throughout the test.
3—An isoprene solution containing 2% by weight of an inhibitor composition (A, B or C) is introduced at a flow rate equal to 1.1 ml/min.
4—The isoprene stream exiting the column is adjusted so as always to maintain at the same level the isoprene solution entering the column.

A sample of isoprene solution exiting the column is taken regularly so as to analyze it by high-performance liquid chromatography (HPLC). The amount of inhibitor composition, in particular of 4-TBC, in the isoprene solution collected is thus measured over time. The time from which the amount of 4-TBC increases substantially in the analyzed isoprene solution corresponds to a rupture point beyond which the alumina begins to no longer fulfil its role as adsorbent.

The results obtained with the inhibitor compositions A, B and C are given in Table 3 below.

TABLE 3 performance in removing the inhibitor compositions A, B and C by adsorption on alumina

| Inhibitor composition | A (invention) | B (comparative) | C (comparative) |
| --- | --- | --- | --- |
| Rupture point (time) | 1.66 T | T | T |

Beyond the time T, the inhibitor compositions B and C are no longer efficiently adsorbed on the alumina.

The results demonstrate that the absorption capacity of the alumina is substantially higher by using the inhibitor composition A. Thus, the regeneration of the alumina may be further spaced out and the lifetime of the adsorbent is extended by using the inhibitor composition A.

The invention claimed is:

1. A composition for inhibiting the polymerization of ethylenically unsaturated monomers, comprising:
   at least 98% by weight of 4-tert-butylcatechol from 0.03% to 0.2% by weight of catechol, and
   at least one impurity selected from the group consisting of 3-tert-butylcatechol, tert-butylhydroquinone and 3,5-di-tert-butylcatechol and mixtures thereof,
wherein the composition comprises, based on the weight of the composition, a total amount of from 0.1% to 0.8% by weight of the catechol and at least one impurity.

2. The composition as claimed in claim 1, wherein the composition comprises from 0.02% to 0.1% by weight 3-tert-butylcatechol.

3. The composition as claimed in claim 1, wherein the composition comprises from 0.03% to 0.1% by weight catechol.

4. The composition as claimed in claim 1, wherein the composition comprises from 0.003% to 0.005% by weight tert-butylhydroquinone.

5. The composition as claimed in claim 1, wherein the composition comprises from 0.1% to 0.6% by weight 3,5-di-tert-butylcatechol.

6. The composition as claimed in claim 1, wherein the composition comprises from 0.15% to 0.5% by weight 3,5-di-tert-butylcatechol.

7. The composition as claimed in claim 1, further comprising one or more additives selected from the group consisting of dispersants, detergents, antioxidants, antifoams, rust inhibitors and corrosion inhibitors.

8. A solution for inhibiting the polymerization of ethylenically unsaturated monomers, comprising the composition as claimed in claim 1 and at least one solvent.

9. The solution as claimed in claim 8, wherein the solvent is chosen from the group consisting of methanol, water and toluene, and mixtures thereof.

10. A mixture comprising an ethylenically unsaturated monomer and the composition as claimed in claim 1.

11. The mixture as claimed in claim 10, wherein said monomer is chosen from the group consisting of monoolefins and diolefins, vinyl monomers, cyclopentadiene, and dicyclopentadiene.

12. A process, comprising removing the 4-tert-butylcatechol, catechol, and at least one impurity from the mixture as claimed in claim 10.

13. The process as claimed in claim 12, wherein said removing comprises placing said mixture in contact with at least one solid inorganic oxide.

14. The process as claimed in claim 12, wherein said removing comprises washing said mixture with an alkaline solution.

15. The process as claimed in claim 12, wherein said removing comprises distilling said mixture.

16. A process for polymerizing the ethylenically unsaturated monomers of a mixture according to claim 10, comprising removing the 4-tert-butylcatechol, catechol, and at least one impurity from the mixture, followed by initiating polymerization of the ethylenically unsaturated monomers.

17. The process of claim 16, wherein the step of removing comprises placing said mixture in contact with at least one solid inorganic oxide, or washing said mixture with an alkaline solution, or distilling said mixture.

\* \* \* \* \*